United States Patent

Yang et al.

[11] Patent Number: 5,985,912
[45] Date of Patent: Nov. 16, 1999

[54] 4-HYDROXY COUMARIN DERIVATIVES

[75] Inventors: Bingwei Yang, Waterford; Joyce Sutcliffe, Clinton, both of Conn.; Chris J. Dutton, Sandwich, United Kingdom

[73] Assignee: Pfizer Inc., New York, N.Y.

[21] Appl. No.: 09/157,128

[22] Filed: Sep. 18, 1998

Related U.S. Application Data

[62] Continuation of application No. 08/771,184, Dec. 20, 1996, abandoned, which is a division of application No. 08/403,818, filed as application No. PCT/US93/06308, Jul. 7, 1993, Pat. No. 5,624,951.

[51] Int. Cl.⁶ .......... A61K 31/35; A61K 31/40; C07D 311/08; C07D 405/12
[52] U.S. Cl. .......... 514/422; 514/457; 548/525; 549/285; 549/287; 549/289
[58] Field of Search .................. 514/422, 457; 548/525; 549/285, 287, 289

[56] References Cited

U.S. PATENT DOCUMENTS

| | | | |
|---|---|---|---|
| B 587,786 | 2/1976 | Pankavich | 424/281 |
| 2,127,879 | 8/1938 | Martin | 167/37 |
| 3,122,557 | 2/1964 | Mohlo | 260/295 |
| 3,509,177 | 4/1970 | McIntyre et al. | 260/343.2 |
| 3,511,856 | 5/1970 | McIntyre et al. | 260/343.2 |
| 3,511,892 | 5/1970 | McIntyre et al. | 260/343.2 |
| 3,991,204 | 11/1976 | Pankavich | 424/281 |
| 4,078,075 | 3/1978 | Beringer | 242/281 |
| 4,128,563 | 12/1978 | Sebek et al. | 260/343.45 |
| 4,148,992 | 4/1979 | Sebek et al. | 536/13 |

FOREIGN PATENT DOCUMENTS

| | | |
|---|---|---|
| 0014372 | 1/1980 | European Pat. Off. . |
| 0038427 | 10/1981 | European Pat. Off. . |
| 0241834 | 10/1987 | European Pat. Off. . |
| 06083 | 4/1992 | European Pat. Off. . |
| 2325324 | 9/1976 | France . |
| 2325650 | 9/1976 | France . |
| 2643428 | 4/1977 | Germany . |
| 2643476 | 4/1977 | Germany . |
| 4668 | 2/1967 | Japan . |
| 26427 | 8/1974 | Japan . |

OTHER PUBLICATIONS

Chem Abstracts, vol. 67: 90675j (1967).
Chem Abstracts, vol. 67: 90676k (1967).
Pharmazie, vol. 39, pp. 86–91 (1984).
J. Org. Chem., vol. 39, No. 7, pp. 1008–1009 (1974).
J. Het. Chem., vol. 9, pp. 495–499 (1972).
Monastsh. Chem., vol. 101, pp. 88–91 (1970).
Chim. Ther., No. 6, pp. 430–440 (1967).
Can. J. Chem., vol. 45, pp. 767–771 (1967).

*Primary Examiner*—Ba K. Trinh
*Attorney, Agent, or Firm*—Peter C. Richardson; Paul H. Ginsburg; Jacob M. Levine

[57] ABSTRACT

Compounds of the formula

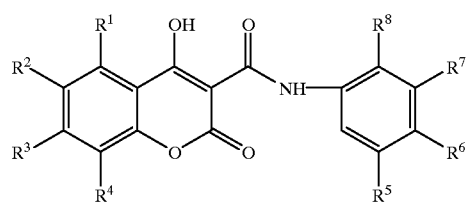

The compounds are useful in the treatment of bacterial infections.

6 Claims, No Drawings

4-HYDROXY COUMARIN DERIVATIVES

This is a continuation of application Ser. No. 08/771,184, filed on Dec. 20, 1996, now abandoned which in turn is a divisional application of Ser. No. 08/403,818, filed on Mar. 1, 1995 now U.S. Pat. No. 5,624,951, which in turn, is the National Phase PCT/US93/06308 filed Jul. 7, 1993, which in turn is the international application of priority application Ser. No. 07/938,701, filed Sep. 1, 1992 now abandoned.

The present application relates to 4-hydroxycoumarin derivatives and pharmaceutical compositions comprising such compounds. The compounds are useful as antibacterial agents.

U.S. Pat. No. 4,078,075 refers to a 3-N-(4-trifluoromethylphenyl)carbamoyl-4-hydroxy-coumarin compound useful in combating insect pests particularly of the species *Heliothis virescens*.

U.S. Pat. No. 3,511,892 refers to a 3-(4-aminophenyl)carbamoyl-4-hydroxycoumarin compound useful as bactericides and fungicides for the control of a wide variety of organisms such as *Staphylococcus aureus, Bacillus substilis, Mycobacterium phlet, Salmonella typhosa, Aerobacter aerogenes, Escherichia coli, Trichophyton mentagrophytes, Pullularia pullulans* and *Cundida alpicans* and other fungal organisms such as downey mildew and tomato late blight.

U.S. Pat. No. 3,112,557 refers to 4,5,7-trihydroxycoumarin-3-N-phenylcarboxamide and 4-hydroxy-6-methyl-2-alpha-pyrone-3-(N-p-hydroxyphenyl)carboxamide, 4-hydroxy-5:6-benzo-2-alpha-pyrone-3-(N-p-hydroxyphenyl)carboxamide compounds useful for their antibacterial or fungicidal activity in human or veterinary therapy.

The present invention relates to compounds of the formula

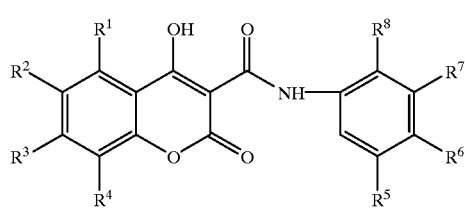

V wherein $R^1$ is hydrogen, $(C_1-C_6)$alkyl or halogen; $R^2$ is hydrogen, halogen, nitro, amino, $(C_1-C_6)$alkoxy or $(C_1-C_6)$alkylthio; $R^3$ is hydrogen, halogen, hydroxy, nitro, amino or $(C_1-C_6)$alkoxy; $R^4$ is hydrogen, halogen, $(C_1-C_6)$alkyl, $(C_1-C_6)$alkoxy, amino or nitro; $R^5$, $R^6$, $R^7$, and $R^8$ are each independently selected from the group consisting of hydrogen, halogen, $(C_1-C_6)$alkenyl, $(C_1-C_6)$alkyl, $(C_1-C_6)$haloalkyl, $(C_1-C_3)$alkoxy, phenyl$(C_1-C_6)$alkoxy, $(C_2-C_8)$acyl, $(C_1-C_6)$thioalkoxy, pyrrolyl, 2,5-dimethylpyrrolyl, imidazolyl, pyridinyl, pyrimidinyl or pyrazinyl with the proviso that when $R^5$ is other than acyl, pyrrolyl, $(C_1-C_3)$alkoxy or 2,5-dimethylpyrrolyl, or $R^8$ is trifluoromethyl, at least one of $R^1$, $R^2$, $R^3$ and $R^4$ is not hydrogen.

More specific compounds of formula V are those wherein at least one of $R^5$, $R^6$, $R^7$, and $R^8$ is halogen, hydroxy, acyl or nitro, and at least one of $R^1$, $R^2$, $R_3$ and $R^4$ is not hydrogen, halogen, hydroxy or nitro.

Preferred compounds of the invention include 4-hydroxy-3-[4'-chlorophenyl)carbamoyl-4-hydroxy-6-methoxycoumarin, 4-hydroxy-3-[4'-methoxy-3'-(3"-methyl-2"-butenyl)phenyl]carbamoylcoumarin, 4-hydroxy-3-(4'-pyrrolyl-3'-trifluoromethylphenyl)carbamoylcoumarin, 7-chloro-4-hydroxy-3-(4'-trifluoromethylphenyl)carbamoylcoumarin.

More specific compounds of formula V are those wherein $R^6$ is pyrrolyl, 2,5-dimethylpyrrolyl, imidazolyl, pyridinyl, pyrimidinyl or pyrazinyl.

More specific compounds of formula V are those wherein $R^1$, $R^2$, $R^4$, $R^5$ and $R^8$ are hydrogen; those wherein $R^3$ is hydrogen or chloro; those wherein $R^6$ is trifluoromethyl, 2,5-dimethylpyrrolyl, pyrrolyl or methoxy and $R^7$ is hydrogen, trifluoromethyl or 3-methyl-2-butenyl.

More specific compounds of formula V are those wherein $R^1$, $R^2$, $R^4$, $R^5$ and $R^8$ are hydrogen.

The present invention also relates to an antibacterial composition comprising a compound of the formula V wherein $R^1$ is hydrogen, $(C_1-C_6)$alkyl or halogen; $R^2$ is hydrogen, halogen, nitro, amino, $(C_1-C_5)$alkoxyl or $(C_1-C_5)$alkylthio; $R^3$ is hydrogen, halogen, hydroxy, nitro, amino or $(C_1-C_5)$alkoxy; $R^4$ is hydrogen, halogen, $(C_1-C_6)$alkyl, $(C_1-C_5)$alkoxy, amino or nitro; $R^5$, $R^6$, $R^7$, and $R^8$ are each independently selected from the group consisting of hydrogen, halogen, $(C_1-C_5)$alkenyl, $(C_1-C_6)$alkyl, $(C_1-C_6)$haloalkyl, $(C_1-C_3)$alkoxy, phenyl$(C_1-C_6)$alkoxy, $(C_2-C_8)$acyl, $(C_1-C_6)$thioalkoxy, pyrrolyl, 2,5-dimethylpyrrolyl, imidazolyl, pyridinyl, pyrimidinyl or pyrazinyl with the proviso that when $R^6$ is other than acyl, pyrrolyl, $(C_1-C_3)$alkoxy, or 2,5-dimethylpyrrolyl, at least one of $R^1$, $R^2$, $R^3$ and $R^4$ is not hydrogen, in an amount effective for treatment of a bacterial infection, and a pharmaceutically acceptable carrier.

The present invention also relates to a method of treating a host affected by a bacterial infection which comprises administering to said host an antibacterial effective amount of a compound of formula V wherein $R^1$, $R^2$, $R^3$, $R^4$, $R^5$, $R^6$, $R^7$ and $R^8$ are as defined for said antibacterial composition.

The following reaction schemes illustrate the preparation of the compounds of the present invention.

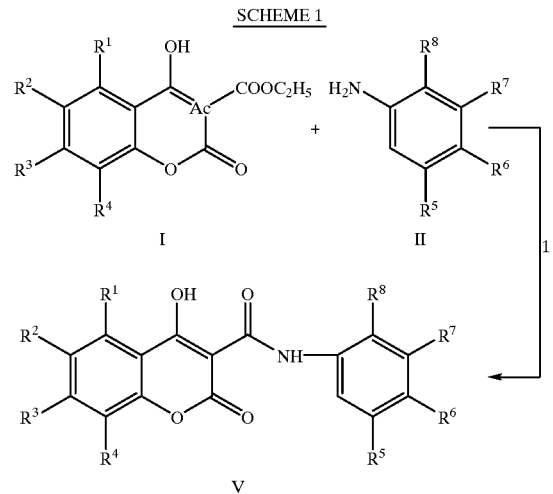

SCHEME 2

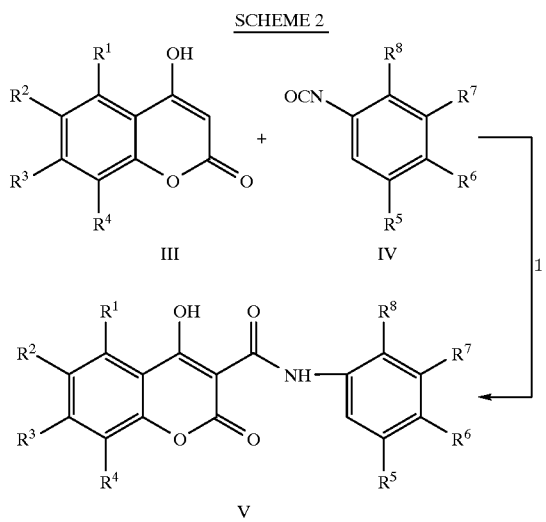

In Scheme 1, the 3-ethylcarboxy-4-hydroxycoumarin compound of formula I is converted to the corresponding 3-carbamoyl-4-hydroxycoumarin of formula V by reacting I with an aniline compound of formula II. The solvent used should be a polar aprotic solvent such as N,N-dimethylformamide, methyl sulfoxide, acetonitrile or nitrobenzene, preferably nitrobenzene. The reaction may be conducted at a temperature between about 80° C. to about 180° C., preferably about 150° C., and preferably for a time period between about 2 hours to about 6 hours, more preferably about 4 hours.

In Scheme 2, the 4-hydroxycoumarin compound of formula III is converted to the corresponding 3-carbamoyl-4-hydroxycoumarin of formula V by reacting III with a phenylisocyanate compound of formula IV in the presence of a base, such as pyridine, 4-dimethylaminopyridine, or a trialkylamine. The preferred trialkylamine is triethylamine. The solvent used is a polar aprotic solvent such as N,N-dimethylformamide, methyl sulfoxide or nitrobenzene, preferably nitrobenzene. The reaction temperature will generally be in the range of about 140° C. to about 180° C., preferably about 160° C., and preferably for a time period of about 14 hours to about 20 hours, more preferably about 17 hours. When the desired product of formula V has a hydroxy group in the 7-position, it is necessary that the 4-hydroxycourmarin compound of formula III be protected, e.g., by using 7-benzyloxy-4-hydroxy-8-methylcoumarin or 4-hydroxy-7-methoxy-8-methylcoumarin, requiring an additional synthetic step for removal of said protecting group. When a benzyloxycoumarin is used, the protecting group may be removed through treatment with an acidic reagent or hydrogenation in the presence of a catalytic amount of palladium on carbon. The preferred reagent is hydrobromic acid in acetic acid. The reaction mixture is refluxed at a temperature between about 80° C. to about 120° C., preferably about 100° C., and preferably for a time period between about 10 hours to about 20 hours, more preferably about 18 hours. When a methoxycoumarin compound is used, the methoxy group may be converted to the corresponding hydroxy compound by treating the compound of formula V so formed with a thioalkoxide ion formed from a base and alkylthiol in a polar aprotic solvent such as N,N-dimethylformamide. The preferred base is sodium hydride and the preferred alkylthiol is ethanethiol. The reaction mixture is heated between about 80° C. to about 120° C., preferably about 100° C., preferably for a time period between about 2 hours to about 5 hours, more preferably about 3.5 hours.

The compounds of formula V are useful in the treatment of bacterial infections of broad spectrum, particularly the treatment of infection by gram-positive bacterial strains.

The compounds V of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1–50 mg/kg/day, advantageously 0.2–10 mg/kg/day given in a single daily dose or up to 3 divided doses.

The invention also provides pharmaceutical compositions comprising an antibacterially effective amount of a compound of the formula (V) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E Steers et al., Antibiotics and Chemotherapy, 9,307 (1959).

The following Examples illustrate the invention.

EXAMPLE 1

8-Chloro-3-[(3'-chlorophenyl)carbamoyl]-4-hydroxy-6-methoxycoumarin

A solution of 8-chloro-3-ethylcarboxy-4-hydroxy-6-methoxycoumarin (0.782 g, 2.62 mmol) and chloroaniline (0.29 ml, 2.74 mmol) in nitrobenzene (10 ml) was heated at 150° C. for 4 hours. After cooling to room temperature, a precipitate was formed. It was filtered and crystallized from methanol to afford the title product as a white solid, mp 249.5–252° C. (248.4 mg, 12.1 mmol, yield 43%). Analysis: Calculated for $C_{17}H_{11}NO_5Cl_2$: C, 53.83; H, 293; N, 3.64. Found: C, 53.39; H, 2.90; N, 6.34. $^1$H NMR (CDCl$_3$): 7.97 (d, J=8.8 Hz, 1H), 7.79 (d, J=1.8 Hz, 1H), 7.42 (d, J=8.4 Hz, 1H), 7.27 (m, 1H), 7.17 (dd, J=8.4, 1.8 Hz, 1H), 6.99 (d, J=8.8 Hz, 1H), 4.04 (s, 3H).

EXAMPLE 2

3-[4'-Methoxy-3'-(3"-methyl-2"-butenyl) phenylcarbamoyl]-4-hydroxycourmarin

To a mixture of 4-hydroxycourmarin (0.162 g, 1.0 mmol) and 4-methoxy-3-(3'-methyl-2'-butenyl)phenylisocyanate (0.217 g, 1.0 mmol) in nitrobenzene (2 ml) was added triethylamine (0.25 ml, 2.47 mmol). The reaction mixture was heated at 160° C. for 17 hours. After cooling to room temperature, a precipitate was formed. The solid was separated by filtration and washed with heptane and methanol obtaining a yellow solid, mp 157–159° C., (85 mg, 0.224 mmol, yield 22.4%). Analysis: Calculated for $C_{22}H_{21}NO_5$: C, 69.66; H, 5.54; N, 3.69. Found: C, 69.56; H, 5.58; N, 3.69. $^1$H NMR (CDCl$_3$): 8.04 (d, J=7.9 Hz, 1H), 7.78 (t, J=9.0 Hz, 1H), 5.28 (br s, 1H), 3.83 (s, 3H), 3.30 (d, J=7.2 Hz), 1.74 (s, 3H), 1.70 (s, 3H).

EXAMPLE 3 TO 11

By the method of Example 2, the following compounds were prepared.

| | R | R6 | R7 |
|---|---|---|---|
| Example 3 | H | Pyrrolyl | CF$_3$ |
| Example 4 | H | 2,5-Dimethyl-pyrrolyl | H |
| Example 5 | 7,8-dimethoxy | CF$_3$ | H |
| Example 6 | 7-Cl | CF$_3$ | H |
| Example 7 | H | COCH$_2$CH$_2$CH$_3$ | H |
| Example 8 | 8-CH$_3$ | CF$_3$ | H |
| Example 9 | 6-Cl | CF$_3$ | H |
| Example 10 | 6-SCH$_3$ | CF$_3$ | H |
| Example 11 | 5-Cl | CF$_3$ | H |

EXAMPLE 3

$^1$H NMR (CDCl$_3$): 15.2 (s, 1H0, 11.5 (s, 1H), 8.10 (m, 2H), 7.90 (dd, J=8.4, 2.4 Hz, 1H), 7.76 (td, J=7.8, 2.4 1H), 7.41 (m, 3H), 6.84 (t, J=2.0 Hz, 2H), 6.33 (t, J=2.0 Hz, 2H).

EXAMPLE 4

$^1$H NMR (CDCl$_3$): 14.8 (s, 1H), 11.4 (s, 1H), 8.10 (dd, J=7.7, 1.4 Hz, 1H), 7.76 (d, J=8.8 hz, 1H), 7.73 (m, 2H), 7.42 (td, J=7.7, 1.4 Hz, 2H), 7.26 (m, 2H), 5.91 (s, 2H), 2.05 (s, 6H).

EXAMPLE 5

$^1$H NMR (CDCl$_3$): 15.1 (s, 1H), 11.4 (s, 1H), 7.82 (d, J=8.9 Hz, 2H), 7.78 (d, J=8.8 Hz, 1H), 7.64 (d, J=8.8 Hz, 2H), 7.00 (d, J=8.8 Hz, 1H), 4.014 (s, 3H), 4.00 (s, 3H).

EXAMPLE 6

$^1$H NMR (CDCl$_3$): 14.7 (s, 1h), 8.04 (d, J=8.3 Hz, 1H), 7.80 (d, J=8.6 Hz, 1H). 7.64 (d, J=8.6 Hz, 1H), 7.43 (m, 2H).

EXAMPLE 7

$^1$H NMR (CDCl$_3$): 15.0 (s, 1H), 11.5 (s, 1H), 8.09 (dd, J=8.2, 1.3 Hz, 1H), 8.01 (d, J=8.8 Hz, 1H), 8.00 (m, 1H), 7.76 (m,2H), 7.744 (m, 2H), 2.94 (t, J=7.4 Hz, 2H), 1.79 (sext., J=7.4 Hz, 2H), 1.02 (t, J=7.4 Hz, 2H).

EXAMPLE 8

$^1$H NMR (CDCl$_3$): 15.1 (s, 1H), 11.5 (s, 1H), 7.92 (dd, J=8.2, 1.1 Hz, 1H), 7.79 (d, J=8.5 Hz, 1H), 7.63 (d, J=8.5 Hz, 1H), 7.58 (d, J=7.7 Hz, 1H), 7.31 (t, J=7.7 Hz).

EXAMPLE 9

$^1$H NMR (CDCl$_3$): 14.9 (s, 1H), 11.4 (s, 1H), 8.05 (d, J=2.6 Hz, 1H), 7.78 (d, J=8.5 Hz, 1H), 7.67 (m, 4H), 7.35 (d, J=8.8 Hz, 1H).

EXAMPLE 10

$^1$H NMR (CDCl$_3$): 15.0 (s, 1H), 11.5 (s, 1H), 7.96 (d, J=2.3 Hz, 1H), 7.80 (d, J=8.6 Hz, 1H), 7.64 (d, J=8.6 Hz, 1H), 7.60 (dd, J=8.8, 2.3 Hz, 1H), 7.31 (d, J=8.8 Hz, 1H).

EXAMPLE 11

$^1$H NMR (CDCl$_3$): 13.9 (s, 1H), 11.5 (s, 1H), 7.78 (d, J=8.8 Hz, 2H), 7.65 (d, J=8.8 Hz, 2H), 7.59 (dd, J=8.4, 7.0 Hz, 1H), 7.44 (d, J=8.4 Hz, 1H).

EXAMPLE 12

A. 7-benzyloxy-4-hydroxy-8-methyl-3-(3"-fluorophenylcarbamoyl)coumarin

According to the procedure of Example 2, 7-benzyl-4-hydroxy-8-methylcoumarin (1.04 g, 3.68 mmol) and 3-fluorophenylisocyanate (0.47 ml, 3.89 mmol) were reacted in the presence of triethylamine (0.05 ml, 0.36 mmol) to generate the title compound as a white solid, mp 219.5–220.5°, (0.63 g, 1.50 mmol, yield 41%). Analysis: Calculated for $C_{24}H_{18}NO_5F$: C, 68.74; H. 4.30; N, 3.34. Found: C, 68.53; H, 4.00; N, 3.30.

B. 4,7-Dihydroxy-8-methyl-3-(3-fluorophenylcarbamoyl)coumarin

To a solution of the compound of Step A (471 mg, 1.12 mmol) in acetic acid (10 ml) was added hydrobromic acid (48%, 5 ml). The mixture was refluxed at 100° C. for 18 hours. After cooling to room temperature, the reaction mixture was poured into water and a precipitate formed. After filtration, the solid was washed with water and then crystallized from dioxane-methanol. The title product was obtained as a white crystalline solid, mp 287–289° C., (94.9 mg, 0.307 mmol, yield 27.4%). Analysis: Calculated for $C_{17}H_{12}NO_5F$: C, 62.01; H, 3.65; N, 4.26. Found: C, 6204; H, 3.65; N, 4.34. $^1$H NMR (DMSO-d$_6$): 7.74 (d, J=8.70 Hz, 1H), 7.65 (d, J=11.3 Hz, 1H), 743 (m, 1H), 7.40 (m, 1H), 7.04 (m, 1H). 6.98 (d, J=8.70 Hz, 1H), 2.26 (s, 3H).

EXAMPLE 13

A. 4-Hydroxy-7-methoxy-8-methyl-3-[4"-methoxy-3-(3"-methyl-2"-butenyl)phenylcarbamoyl]coumarin According to the procedure of Example 2, 4-hydroxy-7-methoxy-8-methylcoumarin (1.66 g. 7.32 mmol) and 4-methoxy-3-(3'-methyl-2'-butenyl)phenylisocyanate (1.59 g. 7.32 mmol) were reacted in the presence of triethylamine (0.2 ml) to generate the title compound, mp 164–166° C. (860 mg, 2.06 mmol, yield 28%). Analysis: Calculated for $C_{24}H_{25}NO_6$: C, 68.08; H, 5.91; N, 3.30 Found:: C, 67.76; H, 5.77; N, 3.38. $^1$H NMR (CDCl$_3$) 7.87 (d. J=8.9 Hz, 1H), 7.47 (dd, J=8.9, 2.4 Hz, 1H), 7.24 (d, J=24 Hz, 1H), 6.88 (d. J=8.9 Hz, 1H), 6.82 (d, J=8.9 Hz, 1H), 5.28 (br t, J=7.2 Hz, 1H), 3.93 (s, 3H), 3.92 (s, 3H), 3.82 (s, 3H), 3.30 (t, J=7.2 Hz, 2H), 2.28 (s, 3H), 1.73 (s, 3H), 1.70 (s, 3H).

B. 4.7-Dihydroxy-8-methyl-3-[(4'-methoxy-3'-(3"-methyl-2"-butenyl)phenylcarbamoyl]coumarin To a sodium hydride (60% dispersion in mineral oil, 254, 6.34 mmol) suspension in N, N-dimethylformamide (DMF, 20 ml) was added ethanethiol (0.48 ml, 6.48 mmol). The mixture was then healed at 100 C. for three and half hours. The cooled mixture was poured into water and was washed with ether. The aqueous layer was acidified with sodium bisulfate to a pH of 4. After extraction with ether twice, the organic layer was washed with brine, dried over magnesium sulfate and upon removal of the solvent afforded a brown solid. This was recrystallized from methanol-ethyl acetate to give the title product as an off-white solid, mp 224–226° C., (78.5 mg, 0.19 mmol, yield 32%). Analysis: Calculated for $C_{23}H_{23}NO_8$: C, 67.47; H, 5.66; N, 3.42. Found: C, 67.64; H, 5.79; N, 3.39. $^1$H NMR (CDCl$_3$): 11.0 (s, 1H), 7.79 (d J=8.8 Hz, 1H), 7.48 (dd, J=8.5, 2.4 Hz, 1H), 7.25 (d, J=2.4 Hz, 1H), 6.88 (d, J=8.5 Hz, 1H), 6.83 (d, J=8.8 Hz 1H), 5.29 (t, J=7.2 Hz, 1H), 3.83 (s, 3H), 3.65 (br s, 1H), 3.31 (d, J=7.2 Hz, 2H), 2.32 (s, 3H), 1.71 (s, 3H), 1.24 (s, 3H).

EXAMPLE 14

4-Hydroxy-3-(2'-trifluoromethylphenylcarbamoyl) coumarin

According to the procedure of example 17, 4-hydroxycoumarin (2.00 g. 12.8 mmol) and 2-trifluoromethylphenylisocyanate(1.93 ml, 12.8 mmol) were reacted in the presence of triethylamine (0.05 ml) to generate the title compound as an off-white solid, mp 157–159° C., (2.2 g, 6.30 mmol, 49.3%). Analysis: Calculated for $C_{17}H_{10}NO_4F_3$: C, 58.45; H, 2.86; N, 4.01. Found: C, 58.47; H, 3.04; N, 4.02. $^1$H NMR (CDCl$_3$): 8.06 (d, J=7.8 Hz, 2H), 7.70 (d, J=8.8 Hz, 2H), 7.62 (t, J=7.8 Hz, 1H), 7.38 (m, 3H).

EXAMPLE 15

A. 7-benzyloxy-4-hydroxy-8-methyl-3-(3'-bromophenylcarbamoyl]coumarin

According to the procedure of example 2, 7-benzyloxy-4-hydroxy-8-methylcoumarin (0.813 g, 2.88 mmol) and 3-bromophenylisocyanate (0.39 ml, 3.12 mmol) were reacted in the presence of triethylamine (0.1 ml) to generate the title compound as an off-white solid, mp 229–231° C., (0.211 g, 0.44 mmol, yield 15.2%). Analysis: Calculated for $C_{24}H_{18}NO_5Br$: C, 601.13; H, 3.76; N, 2.92. Found: C, 60.04; H, 3.51; N, 2.89. $^1$H NMR (CDCl$_3$): 7.94 (br s, 1H), 7.87 (d, J=9.0 Hz, 1H), 7.48 (d, J=7.6 Hz, 1H), 7.41 (m, 5H), 7.24 (m, 2H), 6.97 (d, J=9.0 Hz, 1H), 5.21 (s, 2H), 2.36 (s, 3H).

B. 4,7-Dihydroxy-8-methyl-3-[(3'-bromophenyl) carbamoyl]coumarin

According to the procedure of example 12B, the title compound of step A (0.207 g, 0.43 mmol) was treated with hydrobromic acid (2 ml) in acetic acid (5 ml) to generate the title product as an off-white solid, mp 278° C., (22.9 mg, 0.058 mmol, yield 14%). Analysis: Calculated for $C_{17}H_{12}NO_5Br$: C, 52.33; H, 3.10; N, 3.59. Found: C, 51.93; H, 3.05; N, 3.38. $^1$H NMR (DMSO-d$_6$): 8.19 (br s, 1H), 7.60 (br d, J=8.9 Hz, 1H), 7.30 (br m, 1H), 7.17 (br m, 1H), 7.05 (br m, 1H), 6.66 (br d, J=8.9 Hz, 1H), 2.10 (s, 3H).

EXAMPLE 16

A. 7-benzyloxy4-hydroxy-8methyl-3-(2'-bromophenyl)carbamoyl]coumarin

According to the procedure of example 2, 7-benzyloxy-4-hydroxy-8-methylcoumarin (0.768 g, 2.72 mmol) and 2-bromophenylisocyanate (0.36 ml, 2.88 mmol) were reacted in the presence of triethylamine (0.08 ml) to generate the title compound as a white solid, mp 197–199° C., (0.305 g, 0.63 mmol, yield 23.3%).

B. 4,7-Dihydroxy-8-methyl-3-[(2'-bromophenyl) carbamoyl]coumarin

According to the procedure of example 12B, the title compound of step A (0.308 g, 0.64 mmol) was treated with hydrobromic acid (2 ml) in acetic acid (5 ml) to generate the title product as a white solid, mp 274° C., (147 mg, 0.38 mmol, yield 59%). Analysis: Calculated for $C_{17}H_{12}NO_5Br$: C, 52.33; H, 3.10; N, 3.59. Found: C, 52.13; H, 2.82; N. 3.52.

EXAMPLE 17

4-Hydroxy-6-nitro-3-[(4'-trifluoromethyl)carbamoyl] coumarin

The title compound was prepared by the method of Example 2.

$^1$H NMR (CDCl$_3$): 14.6 (s, 1H), 11.3 (s, 1H), 9.00 (d, J=2.7 Hz, 1H), 8.56 (dd, J=9.1 2.7 Hz, 1H), 7.80 (d, J=8.6 Hz, 2H), 7.68 (d, J=8.6 Hz, 1H). 7.55 (d, J=9.1 Hz, 1H).

We claim:

1. A compound of the formula

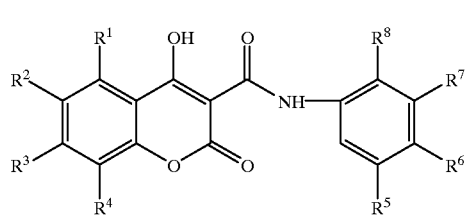

V wherein $R^1$ is hydrogen, $(C_1–C_6)$alkyl or halogen; $R^2$ is hydrogen, halogen, nitro, amino, $(C_1–C_6)$alkoxy or $(C_1–C_6)$alkylthio; $R^3$ is hydrogen, halogen, hydroxy, nitro, amino or $(C_1–C_6)$alkoxy; $R^4$ is hydrogen, halogen, $(C_1–C_6)$alkyl, $(C_1–C_6)$alkoxy, amino or nitro; $R^5$, $R^6$, $R^7$, and $R^8$ are each independently selected from the group consisting of hydrogen, halogen, $(C_1–C_6)$alkenyl, $(C_1–C_6)$alkyl, $(C_1–C_6)$haloalkyl, $(C_1–C_3)$alkoxy, phenyl$(C_1–C_6)$alkoxy, $(C_2–C_8)$acyl, $(C_1–C_6)$thioalkoxy, pyrrolyl, 2,5-dimethylpyrrolyl, imidazolyl, pyridinyl, pyrimidinyl or pyrazinyl; with the proviso that when $R^6$ is other than acyl, or $(C_1–C_3)$alkoxy, or $R^8$ is trifluoromethyl, at least one of $R^1$, $R^2$, $R^3$ and $R^4$ is not hydrogen, and with the proviso that $R^6$ is not pyrrolyl, 2,5-dimethylpyrrolyl, imidazolyl, pyridinyl, pyrimidinyl or pyrazinyl and with the proviso that one of $R^5$–$R^8$ must be —CF$_3$.

2. A compound according to claim 1 wherein at least one of $R^5$, $R^6$, $R^7$, and $R^8$ is halogen, hydroxy, acyl or nitro, and at least one of $R^1$, $R^2$, $R^3$, and $R^4$ is not hydrogen, halogen, hydroxy or nitro.

3. A compound according to claim 1 wherein $R^1$, $R^2$, $R^4$, $R^5$, $R^7$ and $R^8$ are hydrogen; $R^3$ is chloro and $R^6$ is trifluoromethyl.

4. A compound according to claim 1 wherein $R^1$, $R^2$, $R^4$, $R^5$ and $R^8$ are hydrogen.

5. An antibacterial composition comprising a compound of the formula

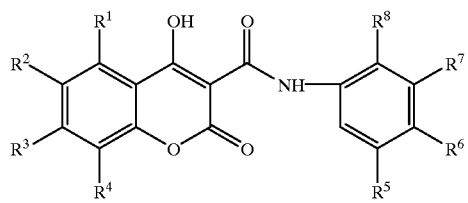

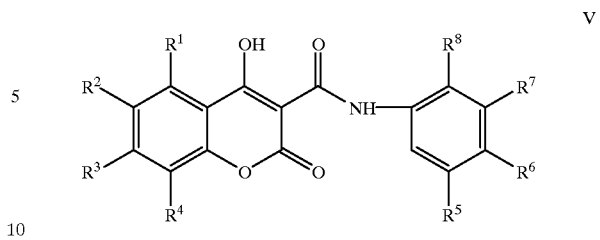

wherein $R^1$ is hydrogen, $(C_1-C_6)$alkyl or halogen; $R^2$ is hydrogen, halogen, nitro, amino, $(C_1-C_6)$alkoxy or $(C_1-C_6)$alkylthio; $R^3$ is hydrogen, halogen, hydroxy, nitro, amino or $(C_1-C_6)$alkoxy; $R^4$ is hydrogen, halogen, $(C_1-C_6)$alkyl, $(C_1-C_6)$alkoxy, amino or nitro; $R^5$, $R^6$, $R^7$, and $R^8$ are each independently selected from the group consisting of hydrogen, halogen, $(C_1-C_6)$alkenyl, $(C_1-C_6)$alkyl, $(C_1-C_6)$haloalkyl, $(C_1-C_3)$alkoxy, phenyl$(C_1-C_6)$alkoxy, $(C_2-C_8)$acyl, $(C_1-C_6)$thioalkoxy, pyrrolyl, 2,5-dimethylpyrrolyl, imidazolyl, pyridinyl, pyrimidinyl or pyrazinyl; with the proviso that when $R^6$ is other than acyl, or $(C_1-C_3)$alkoxy, or $R^8$ is trifluoromethyl, at least one of $R^1$, $R^2$, $R^3$ and $R^4$ is not hydrogen, and with the proviso that $R^6$ is not pyrrolyl, 2,5-dimethylpyrrolyl, imidazolyl, pyridinyl, pyrimidinyl or pyrazinyl and with the proviso that one of $R^5$–$R^8$ must be $CF_3$, in an amount effective for treatment of a bacterial infection, and a pharmaceutically acceptable carrier.

6. A method of treating a host affected by a bacterial infection which comprises administering to said host an antibacterial effective amount of a compound of the formula wherein $R^1$ is hydrogen, $(C_1-C_6)$alkyl or halogen; $R^2$ is hydrogen, halogen, nitro, amino, $(C_1-C_6)$alkoxy or $(C_1-C_6)$alkylthio; $R^3$ is hydrogen, halogen, hydroxy, nitro, amino or $(C_1-C_6)$alkoxy; $R^4$ is hydrogen, halogen, $(C_1-C_6)$alkyl, $(C_1-C_6)$alkoxy, amino or nitro; $R^5$, $R^6$, $R^7$, and $R^8$ are each independently selected from the group consisting of hydrogen, halogen, $(C_1-C_6)$alkenyl, $(C_1-C_6)$alkyl, $(C_1-C_6)$haloalkyl, $(C_1-C_3)$alkoxy, phenyl$(C_1-C_6)$alkoxy, $(C_2-C_8)$acyl, $(C_1-C_6)$thioalkoxy, pyrrolyl, 2,5-dimethylpyrrolyl, imidazolyl, pyridinyl, pyrimidinyl or pyrazinyl; with the proviso that when $R^6$ is other than acyl, or $(C_1-C_3)$alkoxy, or $R^8$ is trifluoromethyl, at least one of $R^1$, $R^2$, $R^3$ and $R^4$ is not hydrogen, and with the proviso that $R^6$ is not pyrrolyl, 2,5-dimethylpyrrolyl, imidazolyl, pyridinyl, pyrimidinyl or pyrazinyl and with the proviso that one of $R^5$–$R^8$ must be —$CF_3$, in an amount effective for treatment of a bacterial infection, and a pharmaceutically acceptable carrier.

\* \* \* \* \*